United States Patent [19]

Kamienski

[11] Patent Number: 4,634,786
[45] Date of Patent: Jan. 6, 1987

[54] HYDROCARBON AND CHLORINATED HYDROCARBON-SOLUBLE MAGNESIUM DIALKOXIDES

[75] Inventor: Conrad W. Kamienski, Gastonia, N.C.

[73] Assignee: Lithium Corporation of America, Gastonia, N.C.

[21] Appl. No.: 655,226

[22] Filed: Sep. 27, 1984

[51] Int. Cl.$^4$ ................................................. C07F 5/06
[52] U.S. Cl. ................................. 556/187; 260/665 R; 568/678; 568/679; 568/851; 556/170
[58] Field of Search ................... 260/448 A, 665 R; 568/678, 679, 851; 556/187, 170

[56] References Cited

U.S. PATENT DOCUMENTS

| | | | |
|---|---|---|---|
| 3,094,546 | 6/1963 | Towers | 568/1 X |
| 3,294,770 | 12/1966 | Ragazzini et al. | 526/344.1 X |
| 3,361,782 | 1/1968 | Liegler et al. | 260/448 A |
| 3,932,545 | 1/1976 | Screttas | 260/665 R |
| 4,027,089 | 5/1977 | Aishima et al. | 260/448 A |
| 4,120,883 | 10/1978 | Sakurai et al. | 260/448 A |
| 4,133,824 | 1/1979 | Malpass et al. | 568/851 X |
| 4,146,549 | 3/1979 | Aishima et al. | 260/448 A |
| 4,410,742 | 10/1983 | Mueller | 568/851 |

Primary Examiner—Helen M. S. Sneed
Attorney, Agent, or Firm—Sidney Wallenstein; Harry V. Strampel

[57] ABSTRACT

Stable liquid hydrocarbon-soluble novel magnesium dialkoxide compositions, and complexes thereof with, for example, n-alkyllithiums, organomagnesiums, and the like, useful as or in the preparation of polymerization catalysts and initiators for the polymerization of alpha-olefins and diolefins, which are prepared, for instance, by reacting certain organomagnesium compounds in liquid hydrocarbon solvents with (a) aliphatic 2-alkyl-substituted $C_4$–$C_{12}$ monohydric primary alcohols, or (b) mixtures of (a) with 2-alkyl-substituted $C_3$–$C_{12}$ aliphatic secondary or tertiary alcohols, or (c) mixtures of (a) with $C_1$–$C_{12}$ aliphatic primary linear alcohols. Such dialkoxides and complexes thereof are commonly advantageously prepared in the presence of minor amounts of organoaluminum, organolithium or organopotassium compounds, e.g., trialkylaluminums, alkyllithiums or potassium dialkoxides. An illustrative example of the novel magnesium dialkoxides is 2-methyl-1-pentyloxide. Illustrative complexes of the said magnesium dialkoxides are those made by mixing n-butyllithium in heptane solution with magnesium 2-methylpentyloxide in heptane solution. Alternatively, 2-alkoxyalkanols, $ROCH_2CHR'OH$, may be used in place of the (a) alcohols, in which case addition of the minor amount of organoaluminum, organolithium or organopotassium compound is not required.

36 Claims, No Drawings

HYDROCARBON AND CHLORINATED HYDROCARBON-SOLUBLE MAGNESIUM DIALKOXIDES

BACKGROUND OF THE INVENTION

This invention is directed to certain novel organomagnesium compounds and processes for making such compounds.

In recent years, certain magnesium alkyl alkoxides and magnesium dialkoxides have been found to possess utility as precursors for magnesium chloride support materials utilized in the preparation of Ziegler-Natta catalysts for alpha-olefin polymerization.

For example, ethylene has been polymerized at 80° C. in hexane using a magnesium alcoholate-TiCL$_4$ reaction product (MgCl$_2$) and a trialkylaluminum as the catalyst system. (M. Bahadir, S. Lutze, W. Payer, P. Schneller, Ger. Offen. No. DE 3,120,186, Dec. 9, 1982 to Ruhrchemie.) In another application, solid magnesium diethoxide, suspended in carbon tetrachloride, is treated with ethyl benzoate and titanium tetrachloride, and the resulting solid product is used in combination with trialkylaluminum and p-methoxybenzoate as a catalyst to polymerize propylene (B. L. Goodall, A. vander Nat, and W. Sjardyn, U.S. Pat. No. 4,414,132, to Shell Oil Co.).

Certain magnesium alkyl alkoxides and dialkoxides have also been generated by reaction of complexed magnesium dialkyls, coated on an inert support material, with an alcohol. These supported magnesium alkoxides are then further reacted with HCl and/or titanium tetrachloride to give a supported magnesium chloride catalyst which can be dried and used to polymerize ethylene (R. Hoff, U.S. Pat. No. 4,402,861 and R. A. Dombro, U.S. Pat. No. 4,378,304 to Chemplex Co.; and M. Bahadir and W. Payer, Ger. Offen. No. DE 3223331, to Ruhrchemie).

Certain magnesium dialkoxides, soluble in hydrocarbon solvents, have known utility for the preparation of MgCl$_2$ which forms a useful support for catalysts to polymerize alpha-olefins, as shown by Goodall (U.S. Pat. Nos. 4,216,383; 4,426,316; and 4,387,200).

D. Gessell (U.S. Pat. Nos. 4,246,383; 4,426,316; and 4,244,838, to Dow Chemical Company) also describes the preparation of a useful alpha-olefin polymerization catalyst by reacting a dialkylmagnesium compound (in the presence of at least 50 mole % of a trialkylaluminum compound) with sufficient n-propyl alcohol to convert all of the alkyl groups to n-propoxy groups, thus forming a hydrocarbon-soluble solution of magnesium and aluminum n-propoxides, followed by reaction of the resulting solution with a titanium ester and a chlorinating agent, ethylaluminum dichloride, to give an MgCl$_2$-supported titanium catalyst.

It is also known to employ a mixture of certain dialkylmagnesiums and either lithium alkoxide, sodium alkoxide or potassium alkoxide in the polymerization and telomerization of butadiene to form low molecular weight liquid polymers, useful in the coating and also in the impregnation and encapsulation of electrical transformers and other metal parts to protect them from corrosion (C. W. Kamienski and J. F. Eastham, U.S. Pat. Nos. 3,742,077; 3,822,219; and 3,847,833). Other patents describing the formation of polymeric products from similar catalyst systems are U.S. Pat. Nos. 4,139,490 and 4,429,090 (to Firestone Tire & Rubber Co.), and U.S. Pat. No. 3,716,495 (to Phillips Petroleum Co.).

A known interchange of alkoxy and alkyl groups occurs on mixing these reagents to yield, in essence, a lithium, sodium or potassium alkyl and a magnesium alkoxide, as shown below:

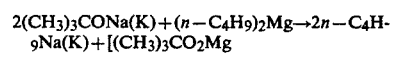

In still another application, a mixture of magnesium isopropoxides and aluminum isopropoxides in tetrahydrofuran (the solubility, if any, unspecified) is reacted with a solution of magnesium aluminum hydride in tetrahydrofuran (THF) to give a solution of magnesium aluminum isopropoxy hydride in THF. (S. Cucinella and G. Dozzi, Ger. Offen. No. DE 3000490, July 31, 1980, to Anic, Sp.A.).

It has, further, been known to the art, as disclosed in U.S. Pat. No. 4,375,564, to dissolve catalytic amounts of magnesium diethoxide and aluminum isopropoxide in a mixture of primary $C_{12}$–$C_{13}$ alcohols, said resulting alcohol mixtures then being ethoxylated with ethylene oxide at a temperature of about 170° C. to form alkanol alkoxylates, which are stated as being useful as nonionic surfactants in detergent formulations.

Although certain magnesium alkyl alkoxides are known to be soluble in hydrocarbon solvents, as described in U.S. Pat. Nos. 4,410,742 and 4,133,824, and by G. E. Coates, J. A. Heslop, M. E. Redwood and D. Ridley, J. Chem. Soc., 1964, 2483 (see also B. J. Wakefield in *Advances in Inorganic Chemistry and Radiochemistry*, Vol. ii, 1968, p. 396 (Academic Press), little is known about the solubility of magnesium dialkoxides. It is known that both magnesium methoxide and ethoxide are insoluble in ethers and hydrocarbon solvents, as described in Kirk Othmer's *Encyclopedia of Chemical Technology*, Vol. 2, p. 12, 3rd Edition, John Wiley, 1978. Magnesium isopropoxide was found by D. Bryce-Smith and B. J. Wakefield (see above) to be insoluble in methylcyclohexane, benzene and ether, and only sparingly soluble in isopropanol. Magnesium t-butoxide is not soluble in ethyl ether (see Coates reference, as well as D. C. Bradley in *Advances in Inorganic Chemistry and Radiochemistry*, Vol. 15, 1972, p. 265 (Academic Press), and, thus, presumably, would be even less soluble in hydrocarbons. Solubility of magnesium alkoxides is not improved by the addition of aluminum alkyls (B. V. Johnson, N. M. Karayannis (EPA No. 95,290, to Standard Oil Company). From the dearth of information on magnesium dialkoxides, it would appear that these materials are, as a class, generally insoluble and intractable in most organic solvents.

C. G. Screttas (U.S. Pat. No. 3,932,545) describes, among other things, the preparation of magnesium 2-ethoxyethoxide in an excess of 2-ethoxyethanol; and, further, its use in dry form as an additive to promote the hydrocarbon solubility of arylmetallics such as phenylsodium, but does not teach its preparation and solubility in hydrocarbon solvents without such additives. (See, also, article in *Organometallics*, Vol. 3, 904–907, 1984).

Schell (U.S. Pat. No. 4,419,269) claims treating R$_2$Mg.xMR′$_x$ with alcohols of the general type R(OR′)$_n$OH and Z(OR′)$_n$OR″)$_{n'}$ in the presence of AL(R$^3$)$_3$mX$_m$, but gives no examples of the use of 2-ethoxyethanol, and also not in the absence of aluminum compounds.

Esnault (U.S. Pat. No. 4,434,282) describes the reaction of DBM with certain diols, e.g., 2-methyl-2,4-pentanediol, 1,8-octanediol and 1,6-hexanediol, but intimates that, in the absence of aluminum alkyls, a "lumpy" product is formed.

Edwards (U.S. Pat. 4,375,564) describes the use of aluminum alkoxides in small quantity (10 mole %) to aid in the solution of magnesium alkoxides in $C_8$–$C_{18}$ alkanols which are used as catalysts to promote the ethoxylation of these alkanols by ethylene oxide.

Aoki et al (U.S. Pat. No. 3,494,896) describe the curing of a mixture of a prepolymer of polyurethane with magnesium propylene glycolate ($Mg(OCH_2CH_2CH_2OH)_2$) as a catalyst to produce an improved sealant, but does not describe the preparation of the magnesium alkoxide nor its state (soluble or not) in the polyurethane composition.

British Pat. No. 870,418 describes the polymerization of monoepoxides in the presence of an aluminum or magnesium alkyl or alkoxide as catalyst.

Magnesium alkoxides of ethylene glycol and 1,2-propanediol are prepared in benzene by reaction with magnesium methoxide, but the resulting product is insoluble (P. Maleki, *Ann. Chem.*, 1977, V. 2, p. 167–175).

It has now been discovered that, under certain conditions, certain magnesium dialkoxides can be prepared directly in liquid hydrocarbon or chlorinated hydrocarbon solvents, and possess a relatively high solubility therein.

Thus, it is one object of my invention to make available magnesium dialkoxides possessing a particularly high solubility in liquid hydrocarbon or chlorinated hydrocarbon solvents, and in the liquid hydrocarbon and chlorinated hydrocarbon solvent solutions thereof.

It is another object of my invention to provide a simplified process for the preparation of such magnesium alkoxides directly in the liquid hydrocarbon or chlorinated hydrocarbon solvents.

Another object of my invention is to prepare liquid hydrocarbon or chlorinated hydrocarbon-soluble stable complexes of magnesium dialkoxides with other metallic alkoxides, such as those of aluminum, boron, zinc, lithium, sodium, potassium, calcium, and barium.

A still further object of my invention is to provide a process for the preparation of liquid hydrocarbon or chlorinated hydrocarbon-soluble stable complexes of these magnesium dialkoxides with alkyllithium, alkylsodium, alkylpotassium, dialkylmagnesium and trialkylaluminum compounds and mixtures thereof.

SUMMARY OF THE INVENTION

In accordance with my invention, certain alcohols are reacted, with magnesium dialkyls or alkylmagnesium dialkoxides in liquid aliphatic or aromatic hydrocarbon or chlorinated hydrocarbon solvent media to form highly soluble, stable solutions of novel and highly useful magnesium dialkoxides.

Whereas, generally speaking linear magnesium primary dialkoxides possess little or essentially no solubility in liquid hydrocarbon or chlorinated hydrocarbon solvents, those with 2-alkyl-substituents in the alcohol moiety of said dialkoxides possess a much higher solubility, especially in the presence of minor amounts of aluminum alkoxides and lithium or potassium alkoxides derived from the same said alcohol moiety; that is, those alcohols with 2-alkyl substituents. Unlike their effect on barium alkoxides of this type (see my copending U.S. patent application Ser. No. 551,917, filed Nov. 15, 1983), chelating tertiary di- or polyamines, such as N, N, N', N'- tetramethylethylenediamine (TMEDA), were found not to enhance the solubility of these magnesium alkoxides.

As was found with respect to the corresponding barium alkoxides, magnesium tert-alkoxides possess a low to intermediate solubility in liquid hydrocarbon or chlorinated hydrocarbon solvents when prepared by the process of my invention:

| Magnesium Alkoxide | Solvent Type | Conc (M) | Physical Description of Reaction Mixture |
|---|---|---|---|
| tert-Butoxide | Cyclohexane | — | Thick slurry forms which sets to solid mass on standing. |
| 3-Methyl-3-Pentyloxide | Heptane-Cyclohexane or Toluene | 0.26 | Solid slurry. |
| tert-Amyloxide | Heptane-Cyclohexane | 0.38 | Solid slurry. |

Unlike the soluble barium secondary alkoxides, magnesium secondary alkoxides were found to be of a low order of solubility in hydrocarbon or chlorinated hydrocarbon solvents:

| Magnesium Alkoxide | Solvent Type | Conc (M) | Physical Description of Reaction Mixture |
|---|---|---|---|
| Isopropoxide | Heptane-Cyclohexane or Toluene | — | Solid gel. |
| sec-Butoxide | Heptane-Cyclohexane | 0.38 | Fluid slurry of fine particles. |
| 4-Methyl-2-Pentyloxide | Cyclohexane | — | Thick gelatinous mass which solidifies on standing. |
| 2,6-Dimethyl-4-Heptyloxide | Heptane-Cyclohexane | 0.44 | Thin suspension of a fine white ppt. |

By contrast, I have determined that 2-alkyl-substituted magnesium primary dialkoxides possess a substantially higher solubility in liquid hydrocarbon or chlorinated hydrocarbon solvents under these reaction conditions:

| Magnesium Dialkoxide | Solvent Type | Conc (M) | Physical Description of Reaction Mixture |
|---|---|---|---|
| 2-Methyl-1-Pentyloxide | Cyclohexane | 1.3[b] | Mobile, water-clear solution. |
| 2-Ethyl-1-Hexyloxide | Cylcohexane | 1.3[b] | Viscous, water-clear solution. |
| 2-Ethyl-4-methyl-1-Pentyloxide | Heptane-Cylcohexane | 0.66[c] | Viscous, water-clear solution. |

Mixtures of these 2-alkyl-substituted magnesium primary dialkoxides and other branched dialkoxides prepared in this manner were also determined by me to possess a substantial solubility in hydrocarbon or chlorinated hydrocarbon solvents:

| Magnesium Alkoxide | Solvent Type | Conc (M) | Physical Description of Reaction Mixture |
|---|---|---|---|
| 2-Methyl-1-Pentyloxide-Isopropoxide (1:1) | Heptane-Cyclohexane | 0.66[b] | Clear, mobile solution. |
| 2-Methyl-1-Pentyloxide-Isobutoxide | Heptane-Cyclohexane | 0.66[b] | Clear, viscous solution. |
| (2:1) 2-Ethyl-1-Butoxide-Isopropoxide (1:1) | Heptane-Cyclohexane | 0.66[c] | Clear, viscous solution. |
| 2-Methyl-1-Pentyloxide-sec-Butoxide (1:1) | Heptane-Cyclohexane | 0.66[b] | Clear, viscous solution. |
| 2-Ethyl-1-Hexyloxide-Isopropoxide (1:1) | Heptane-Cyclohexane | 0.66[b] | Clear, viscous solution. |
| 2-Ethyl-1-Butoxide/sec-Butoxide/2-Methyl-1-Pentyloxide (2:1:1) | Heptane-Cyclohexane | 0.6 | Slightly hazy solution. |

[a]Prepared by slow addition of neat alcohol to either n-butyl-sec-butylmagnesium or di-n-hexylmagnesium in a liquid hydrocarbon solvent.
[b]Not necessarily the upper limit of solubility.
[c]Solubility at 50° C.

In one method of the practice of my invention, a dialkylmagnesium dissolved in a liquid hydrocarbon solvent is treated first with a catalytic amount (about 3 mole %, based on magnesium) of a trialkylaluminum compound, and then with slightly more than twice the molar equivalent, based on magnesium, of a $C_4$–$C_{12}$ 2-alkyl-substituted primary monohydric alkanol or alcohol, or a mixture of these alkanols or alcohols, either neat or in solution in a liquid hydrocarbon or chlorinated hydrocarbon solvent. Alkanes are rapidly generated, and can be driven off by heating to the boiling point if low boiling (ca 0°–5° C.), or absorbed by the solution itself.

In place of part of the 2-alkyl-substituted primary alkanol, secondary alcohols can be used, such as isopropanol or sec-butanol, most favorably, up to about a 1:1 molar ratio, based on the 2-alkyl-substituted primary alkanol, although more may be employed.

The excess of 2-alkyl-substituted primary alkanol employed, over and above twice the molar equivalent (based on magnesium), is generally in the range of 0.01 to 2.0 molar equivalents, based on magnesium, but will more preferably lie in the range of 0.1–1.0 molar equivalents. This addition of an excess of the 2-alkyl-substituted primary alkanol possesses an unusually beneficial action on the viscosity and/or solubility of many of these branched magnesium dialkoxides and mixtures thereof, as shown below:

| Magnesium Dialkoxide | Molar Equiv. ROH Added (on Mg) | Solubility (M) Before ROH Addition | Solubility (M) After ROH Addition | Viscosity Change on ROH Addition |
|---|---|---|---|---|
| 2-Ethylbutoxide-Isopropoxide (1:1) | 0.29[a] | 0.66 at 50° C. | 0.66 (25° C.) | Viscosity decreased significantly |
| 2-Methylbutoxide Isopropoxide (1:1) | 0.34[a] | Heavy slurry (Low solubility) | 0.66 (25° C.) | — |
| 2-Methyl-1-pentyloxide Isopropoxide (1:2) | 0.67[a] | Heavy slurry (Low solubility) | 0.66 (25° C.) (Clear solution) | — |
| 2-Methyl-1-pentyloxide | 0.10[a] | 0.67 | 0.67 | Viscosity decreased significantly |
| 2-Ethyl-1-hexyloxide | 0.47[b] | 0.59 | 0.59 | Viscosity decreased significantly |
| 2-Ethyl-1-butoxide/sec-Butoxide/2-Methylpentyloxide (2:1:1) | 0.25[a] | 0.6 (Hazy solution with some crystals) | 0.66 (Clear solution) | — |

[a]2-Methyl-1-pentanol.
[b]2-Ethyl-1-hexanol.

Although, according to my invention, certain 2-alkyl-substituted primary alkanols, such as 2-methyl-1-pentanol, on reaction with dialkylmagnesium compounds, require the presence of only a very minor proportion (1 to 5 mole %) of a trialkylaluminum, or of an added aluminum trialkoxide or trialkylboron or dialkylzincs, it has been found by me that the presence of substantially greater amounts of these organo-aluminum compounds are required to yield hydrocarbon or chlorinated hydrocarbon solvent-soluble magnesium dialkoxides when employing other alkanols, as shown below:

| Magnesium Dialkoxide | Mole % Al Added (Based on Mg)[a] |
|---|---|
| Magnesium di-(n-Propoxide) | 25[b] |
| Magnesium di-(n-Butoxide) | 23[c] |
|  | 25[b] |
| Magnesium di-(Isobutoxide) | 45[c] |
| Magnesium di-(2-Methyl-1-Butoxide) | 45[c] |
| Magnesium di-(2-Ethyl-4-Methyl-1-Pentyloxide) | 32[c] |
| Magnesium di-(2,6-Dimethyl-4-Heptyloxide) | 20[c] |
| Magnesium n-Butoxide/2-Methyl-1-Pentyloxide | 10[c] |
| Magnesium n-Hexyloxide/2-Methyl-1-Pentyloxide | 7[c] |
| Magnesium n-Octyloxide/2-Methyl- | 7[c] |

| Magnesium Dialkoxide | Mole % Al Added (Based on Mg)[a] |
|---|---|
| 1-Pentyloxide | 5 |

[a] Amount of aluminum compound added sufficient to give clear solution and/or decrease solution viscosity at room temperature.
[b] Aluminum present as TIBAL prior to reaction with alkanol.
[c] Aluminum present as Aluminum 2-Methyl-1-Pentyloxide formed in situ or added separately after reaction with alkanol.

Gessell (see above) does not teach the use, in his catalyst preparations, of minor amounts of aluminum alkoxides to promote the solubility of magnesium alkoxides in liquid hydrocarbon or chlorinated hydrocarbon solvents, nor the use of the much more soluble magnesium 2-alkyl-substituted primary dialkoxides, as is shown in my invention. This is substantiated by his use of at least 50 mole % of aluminum (based on magnesium) and the sole use of n-propanol in the magnesium alkoxide preparative examples shown in his patents. In essence, he discloses the preparation of liquid hydrocarbon-soluble magnesium-aluminum alkoxide complexes, rather than liquid hydrocarbon or chlorinated hydrocarbon solvent-soluble magnesium alkoxides, as shown in my invention. In the preparation of some alpha-olefin $MgCl_2$-based catalyst supports, it is beneficial to have little or no aluminum in the $MgCl_2$ precursor compound. Thus, my invention provides a novel and useful product for such an application.

In place of aluminum alkoxides, one can substitute other metallic alkoxides of Groups I, II and III of the Periodic Table to effect the solubility of magnesium dialkoxides in liquid hydrocarbon or chlorinated hydrocarbon solvents. For example, the addition of as little as 5 mole % of lithium, sodium or potassium 2-methylpentyloxide (based on magnesium) to a gelatinous mixture of magnesium 2-methylpentyloxide in heptane effects the immediate dissolution of the gel and the formation of a clear, mobile solution of the magnesium dialkoxide in the heptane. Other metallic alkoxides which can be used, for example, are those of Na, K, Ca, Ba, B and Zn.

In addition to the 2-alkyl-substituted 1-alkanols shown above, such as, for example, 2-methyl-1-pentanol, it has now also been found possible to employ 2-alkoxy-substituted 1-alkanols, such as 2-methoxy-1-ethanol and 2-ethoxy-1-ethanol, to prepare liquid hydrocarbon or chlorinated hydrocarbon solvent-soluble magnesium 2-alkoxyalkoxides by reaction with suitable magnesium-containing precursors, such as magnesium metal, magnesium amide, dialkylmagnesium compounds and magnesium monoalkoxides, such as magnesium ethoxide. In this modification, no added aluminum, lithium or potassium compounds are necessary to maintain solubility and fluidity of the resulting liquid hydrocarbon or chlorinated hydrocarbon solvent solutions of the magnesium 2-alkoxyalkoxides.

In a novel preparative method in accordance to one particular facet of my invention, the magnesium-2-alkoxyalkoxides are prepared by simple mixing of solid magnesium monoalkoxides, such as magnesium diethoxide, with slightly more than two molar equivalents of the 2-alkoxyalkanol, such as 2-ethoxyethanol, followed by dissolution of the liquid product in the desired hydrocarbon or chlorinated hydrocarbon solvent. Advantages over other processes (including that of the aforesaid Screttas patent) are as follows:

1. My above procedure involves only simple mixing of said components to convert the solid hydrocarbon or chlorinated hydrocarbon-insoluble magnesium monoalkoxides to hydrocarbon or chlorinated hydrocarbon solvent-soluble magnesium-2-alkoxyalkoxides.

2. The process is less expensive and less hazardous than that which uses dialkylmagnesium compounds, as contrasted to a lengthy reaction using magnesium metal in place of the lower magnesium alkoxides.

3. The hydrocarbon or chlorinated hydrocarbon solvent-soluble magnesium-2-alkoxyalkoxides can be prepared from relatively less expensive and generally more readily available starting materials.

4. The magnesium 2-alkoxyalkoxide can be prepared free of hydrocarbon solvent (neat) to give a liquid or fluid product, $Mg(OCH_2CHR'OR)_2 \cdot (R''OH)_x$, in which R and R'' are $C_1-C_{12}$ hydrocarbyl groups and R' is hydrogen or $C_1-C_3$ hydrocarbyl group. (x =0-2). Thus, magnesium 2-ethoxy-ethoxide prepared by reaction of magnesium ethoxide with slightly more than two equivalents of 2-ethoxy-ethanol in the absence of solvents such as heptane or chlorobenzene has been found to be a clear, mobile, liquid product, essentially corresponding to the chemical formula $Mg(OCH_2CH_2OCH_2CH_3)_2 \cdot (CH_3CH_2OH)_2$, a novel product having utility in catalyst ($\alpha$-olefin) preparations. For example, the product can be dispersed in mineral oil and chlorinated to give essentially uniformly-sized particles of magnesium chloride which can serve as a support for a deposited titanium catalyst for alpha-olefin polymerization.

This form of magnesium dialkoxide is totally different from the solid product produced by the above-mentioned Screttas patent, and is also different from the chlorobenzene solution of the magnesium 2-ethoxyethoxide produced by reaction of slightly more than two equivalents of 2-ethoxyethanol with magnesium metal in an essentially neat reaction, followed by dissolution of the resulting product in a minimum of chlorobenzene, according to my invention.

In another novel facet of my present invention, magnesium dialkoxide in a hydrocarbon or chlorinated hydrocarbon solvent-soluble form, when mixed with organolithium, organosodium or organopotassium compounds, form useful telomerization or polymerization initiators.

Additionally, hydrocarbon or chlorinated hydrocarbon solvent-soluble magnesium alkoxides can be readily mixed with hydrocarbon or chlorinated hydrocarbon solvent-soluble magnesium alkyls to form soluble alkylmagnesium dialkoxide which are useful in the preparation of halogen-free Ziegler catalysts which are useful as co-catalysts for the polymerization of olefins, diolefins, or olefin oxides. Such a procedure for forming alkymagnesium alkoxides is deemed superior to that described in either Malpass (U.S. Pat. No. 4,133,824) or Mueller (U.S. Pat. No. 4,410,742 to Schering A.G.) in that no insoluble magnesium alkoxide need be employed which would tend to slow the reaction with dialkylmagnesium compounds or incompletely react therewith. The resulting alkyl-magnesium alkoxides, when complexed with alkali metal alkyls, also form useful initiators for the polymerization of 1,3-dienes and vinylaromatic compounds.

Typical reactions involved in regard to the preparation of the magnesium dialkoxides and complexes thereof with organometallic compounds are shown below:

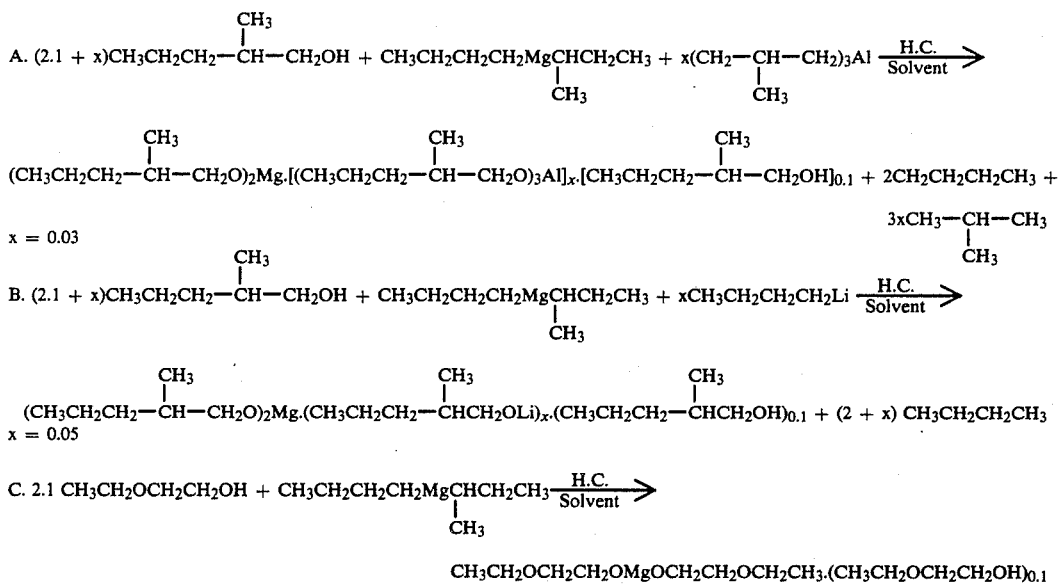

2-alkyl-substituted primary monohydric (normal) alcohols or alkanols (C$_4$–C$_{12}$), which are reacted with dialkylmagnesium compounds in various of the embodiments of my invention, are exemplified by isobutyl alcohol, 2-methyl-1-pentanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, 2-ethyl-5-methyl-1-octanol, and the like, or mixtures thereof. Preferred 2-alkyl-substituted primary monohydric normal alcohols or alkanols are 2-methyl-1-pentanol and 2-ethyl-1-hexanol and mixtures thereof.

Other alcohols, which advantageously can be admixed with the above 2-alkyl-substituted primary alkanols and co-reacted with dialkylmagnesium compounds, are C$_3$–C$_{12}$ aliphatic secondary and tertiary alcohols, notably C$_3$–C$_{12}$ aliphatic secondary or tertiary branched alcohols such as isopropanol, sec-butanol, 4-methyl-2-pentanol, tert-butanol, tert-amylalcohol, 3-methyl-3-pentanol, 2,6-dimethyl-4-heptanol and the like.

Still other alcohols which may be mixed with the above 2-alkyl-substituted primary alcohols and co-reacted with dialkyl-magnesium compounds are C$_1$–C$_{12}$ aliphatic primary (linear, unsubstituted) alcohols, such as, for example, methanol, ethanol, n-butanol, n-hexanol, n-octanol and the like. The amounts of said primary (unsubstituted) secondary and tertiary alcohols which are coreacted with said C$_4$–C$_{12}$ 2-alkyl-substituted primary alcohols may be varied from 0.1 to 2 moles per mole of said C$_4$–C$_{12}$ 2-alkyl-substituted primary alcohols, but will preferably be in the range of 0.5 to 1 mole per mole of said alcohol, and most favorably in the range of 0.7 to 1 mole per mole of said alcohol.

In addition to the alcohols mentioned above, which can be coacted with dialkylmagnesium compounds, are 2-alkoxy-1-alkanols, ROCH$_2$CHR'OH (R is C$_1$–C$_{12}$ hydrocarbyl and R' is hydrogen or C$_1$–C$_3$ hydrocarbyl), such as, for example, 2-methoxy-1-ethanol, 2-ethoxy-1-ethanol, 2-butoxy-1-ethanol, 2-butoxy-1-methyl-1-ethanol, 2-hexyloxy-1-ethanol, and the like, commonly referred to in the art as "Cellosolve" solvents (Union Carbide Corp.).

Analogous to the "Cellosolve" solvents are the so-called "Carbitols" (Union Carbide Corp.) such as, for example, 2-ethoxyethoxyethanol and 2-butoxyethoxyethanol. In general, these are alcohols of the type belonging to the generic group of γ-alkoxy (polyethyleneoxy)-1-ethanols, RO(CH$_2$CH$_2$O)$_n$CH$_2$CH$_2$OH, where R is a C$_1$–C$_{12}$ hydrocarbyl group, but most desirably ethyl, n-butyl and n-hexyl, and n may vary from 0 to 4. One can also employ mixtures of these alcohols with each other and the monohydric alcohols described above in the proportions given therein.

Advantageously, an excess of the alcohol or mixture of alcohols, above that necessary to react with all of the dialkylmagnesium present, is employed in order to gain an increased fluidity or solubility of the resulting magnesium alkoxide in hydrocarbon or chlorinated hydrocarbon solution. This excess of alcohol can vary from 0.01 to 2 moles of alcohol per mole of magnesium reacted, but preferably varies from 0.05 to 1 mole of alcohol per mole of magnesium reacted, and most advantageously from 0.1 to 0.5 moles of alcohol per mole of magnesium reacted. The said alcohols can be added to the dialkylmagnesium compounds in either neat form or dissolved in a liquid hydrocarbon or chlorinated hydrocarbon solvent of choice.

In those cases where lower magnesium dialkoxides (C$_1$–C$_3$) are reacted with two molar equivalents of 2-alkoxy-1-alkanols, ROCH$_2$CHR'OH, two molar equivalents of the C$_4$–C$_3$ lower alcohol are generated per magnesium 2-alkoxy-1-alkoxide formed and, beneficially, promote the solubility of the said dialkoxides.

The dialkylmagnesium compounds employed in the reaction with the above alcohols can be varied widely. For convenience, they are generally soluble in liquid hydrocarbon or chlorinated hydrocarbon media, although it is not outside the scope of this invention to employ dialkylmagnesium compounds or diarylmagnesium compounds which are insoluble in liquid hydrocarbon or chlorinated hydrocarbon media. Included are typical dialkylmagnesiums, such as n-butyl-sec-butylmagnesium, n-butyl-ethylmagnesium, di-n-hexylmagnesium, diisopropylmagnesium, di-n-butylmagnesium, di-sec-butylmagnesium, di-2-methyl-butylmagnesium, di-n-amylmagnesium, n-butyl-n-octylmagnesium, ethylisoamyl-magnesium, and typical diarylmagnesium compounds, such as diphenylmagnesium, phenylmagnesium chloride and the like.

These dialkylmagnesium compounds can also contain sufficient added trialkylaluminum compounds to maintain solubility and fluidity of the resulting magnesium alkoxides in the liquid hydrocarbon or chlorinated hydrocarbon solutions after reaction with the desired alcohols. It is, in any case, preferred that such trialkylaluminum compounds be added to the said dialkylmagnesium compounds, when not originally present, prior to reaction with said alcohols. Generally, amounts of trialkylaluminum to be added or maintained can be varied from 0.005 to 2 moles per mole of magnesium compound, but are preferably in the range of 0.01 to 1 mole per mole of magnesium compound, and most advantageously in the range of 0.02 to 0.1 mole of trialkylaluminum per mole of dialkylmagnesium compound. Typical trialkylaluminum compounds employable are triethylaluminum, tri-isobutylaluminum, tri-n-butylaluminum, tri-n-hexylaluminum, diethyl-n-butylaluminum, tri-n-octylaluminum, and the like. Instead of adding the trialkylaluminum to the . dialkylmagnesium compound prior to reaction with desired alcohol, aluminum trialkoxide or trialkylaluminum can be added after reaction of the alcohol with the dialkylmagnesium is complete and then further reacted with alcohol, if required.

In place of the trialkylaluminum compounds mentioned above, which are added to the dialkylmagnesium compounds prior to reaction with the desired alcohols, there can be added other organometallic compounds or metallic alkoxides such as trialkylboron, dialkylzinc, alkyllithium, alkylsodium, potassium alkoxide, sodium alkoxide, calcium alkoxide, and barium alkoxide compounds and the like to maintain solubility and fluidity of the resulting magnesium dialkoxides in the liquid hydrocarbon or chlorinated hydrocarbon solvent solutions. Other compounds containing said metals can be added, as well, which are reactive with the added alcohol, as, for example, sodium amide, sodium hydride, potassium hydride, calcium amide, barium amide, and the like. Generally, amounts of added organometallic compound, metallic alkoxide or other metal derivative can be varied in the range of 0.005 to 2 moles per mole of magnesium compound, but are preferably in the range of 0.01 to 1 mole per mole of magnesium compound, and most advantageously in the range of 0.02 to 0.1 mole of organometallic compound, metallic alkoxide, or metal derivative per mole of dialkylmagnesium compound.

Typical organometallic compounds employable are methyllithium, n-butyllithium, sec-butyllithium, tert-butyllithium, phenyllithium, phenylsodium, n-amylsodium, triethylboron, tri-n-butylboron, diethylzinc, di-n-butylzinc, and the like, and mixtures thereof.

Typical metallic alkoxides employable are lithium tert-butoxide, lithium 2-methyl-1-pentyloxide, lithium sec-butoxide, sodium tert-butoxide, sodium tert-amyloxide, sodium 2-methyl-1-pentyloxide, potassium tert-butoxide, potassium tert-amyloxide, potassium 2-methyl-1-pentyloxide, calcium 2-ethyl-1-hexyloxide, calcium 2-methyl-1-pentyloxide, barium 2-ethyl-1-hexyloxide, barium 2-methyl-1-pentyloxide, tri-n-butoxyboron, tri-2-methyl-1-pentyloxyboron, zinc di-2-methyl-1-pentyloxide, and the like, and mixtures thereof.

It is generally preferable (although not essential) to add organometallic compounds or metallic alkoxides which are soluble in the liquid hydrocarbon or chlorinated hydrocarbon medium employed.

It is also within the scope of my present invention to react the said alcohols used in accordance with my invention with magnesium compounds other than dialkylmagnesiums. For example, magnesium amide, $Mg(NH_2)_2$, can be reacted with said alcohols in a liquid hydrocarbon medium in a manner similar to that described for the production of barium alkoxides from barium amide in my aforementioned copending application. Other methods include reaction of said alcohols with magnesium metal or magnesium hydride, transalcoholysis of lower $C_1$–$C_3$ magnesium alkoxides with said alcohols, or reaction of the alkali metal alkoxide derivatives of said alcohols with magnesium halide salts. It is, further, within the scope of my present invention to react Grignard reagents, RMgX, with said alcohols to produce useful dialkoxymagnesium compounds. Obviously, for optimal economy in the production of the resulting magnesium dialkoxides, the lowest priced magnesium compounds (coupled with the simplest process parameters) will be most advantageous.

The reaction of the aforementioned alcohols, used in accordance with my present invention, with dialkylmagnesium compounds can be carried out at any convenient temperature. Generally, it is preferred to carry out the reaction at lower temperatures, i.e., below the boiling point of the liquid hydrocarbon or chlorinated hydrocarbon solvent employed. The said alcohols can be added to the dialkylmagnesium compound, or vice versa. Addition is generally carried out incrementally.

A wide variety of liquid hydrocarbon and chlorinated hydrocarbon solvents can be employed in the practice of my invention. Generally, such solvents employed are the ones in which the dialkylmagnesium solutions are sold commercially. However, as mentioned above, additional solvents of choice can be added as diluents for the reactive alcohol. Aliphatic or cycloaliphatic solvents, such as, for example, isopentane, n-pentane, n-hexane, n-heptane, cyclohexane, methylcyclohexane, and the like, are preferred. However, aromatic solvents can also be employed, such as, for example, benzene, toluene, xylene, mesitylene, and the like, or mixtures thereof with aliphatic or cycloaliphatic solvents. Among the illustrative liquid chlorinated hydrocarbon solvents are 1,1,1-trichloroethane; 1,1-dichlorobutane; 1,4-dichlorobutane; 1-chlorohexane; chlorocyclohexane; mono- and polychlorobenzenes; 3,4-di-chlorotoluene; 1-chloropentane; 1,3-dichlorohexane; dichlorofluoromethane; trichlorofluoromethane; and the like.

It is also within the scope of my invention to employ minor quantities of ethereal solvents in the formulation of the magnesium dialkoxide solutions, such as, for example, diethyl ether, THF, methyl tert-butyl ether, di-n-butyl ether and the like, or monofunctional tertiary amines, such as, for example, trimethylamine, triethylamine, N-methylpiperidine and the like. Other co-solvents, compatible with magnesium dialkoxide, can also be employed, such as, for example, chlorobenzene, carbon tetrachloride, chloroform, dimethylacetamide, dimethylformamide, hexamethylphosphorus triamide, and the like.

Various organometal reagents can be admixed with the aforesaid liquid hydrocarbon-soluble magnesium dialkoxides of my present invention to form novel hydrocarbon-soluble organometallic complexes. Within the scope of my invention is the use of organolithium compounds generally soluble in hydrocarbon media, such as ethyllithium, isopropyllithium, n-hexyllithium, n-octyllithium and mixtures of these, such as n-butyllithium and ethyllithium, to form novel products soluble in liquid hydrocarbon solvents.

Other organoalkali compounds not normally soluble in liquid hydrocarbon or chlorinated hydrocarbon solvents can also be admixed with the magnesium dialkoxides of my present invention, including, for example, n-butylsodium, n-butylpotassium, n-amylsodium, n-hexylsodium, n-hexylpotassium and the like, and mixtures of these with organolithium compounds in the range of 0.01 to 10 moles per mole of magnesium alkoxide, but more preferably in the range of 0.05 to 2 moles per mole of magnesium alkoxide.

In place of, or in admixture with, the organolithium or other organoalkali compounds, one can employ diorganomagnesium compounds soluble in liquid hydrocarbon or chlorinated hydrocarbon media for interaction with the magnesium dialkoxides of my invention. Examples of these diorganomagnesium compounds are diethylmagnesium, n-butyl-ethylmagnesium, diisopropylmagnesium, n-butyl-sec-butylmagnesium, n-butyl-n-octylmagnesium, di-n-hexylmagnesium, di-sec-butylmagnesium, di-2-methylbutylmagnesium and di-n-octylmagnesium, and the like, and mixtures thereof. Products formed by this interaction are alkylmagnesium alkoxides, which also can be formed by adding only one-half the stoichiometric amount of the alcohol to a dialkylmagnesium compound, according to my invention.

In admixture with the magnesium dialkoxides of my present invention are also included triorganoaluminum compounds normally soluble in liquid hydrocarbon or chlorinated hydrocarbon media, such as TIBAL, triethylaluminum, tri-n-butylaluminum, tri-n-hexylaluminum and tri-n-octylaluminum and the like, and mixtures thereof in the range of 0.01 to 10 moles per mole of magnesium alkoxide, but more preferably in the range of 0.05 to 2 moles per mole of magnesium dialkoxide.

The following Examples are illustrative of various facets of my present invention, showing the preparation of novel, stable liquid hydrocarbon or chlorinated hydrocarbon solvent-soluble magnesium dialkoxides. It will, of course, be understood that many other novel, stable liquid hydrocarbon or chlorinated, hydrocarbon solvent-soluble magnesium dialkoxides can be made pursuant to my present invention, utilizing different magnesium dialkoxides; different complex-forming solubilizers; and different organometallics than the particular alkyllithiums, dialkylmagnesiums or trialkylaluminums used in the Examples; different liquid hydrocarbon solvents, or chlorinated hydrocarbon solvents; and different reaction temperatures, etc., without departing from the guiding principles and teachings disclosed therein. All temperatures recited are in degrees Centigrade.

EXAMPLE I

Preparation of Hydrocarbon-Soluble Magnesium 2-Methyl-1-Pentyloxide (Pentanolate)

(a) To a volume of 100 ml of 1.024 Molar n-butyl-sec-butyl-magnesium in heptane (DBM, Lithium Corporation of America) is added 3.3 ml of 0.92 Molar TIBAL in heptane (Texas Alkyls, Inc.).

To the stirred solution cooled in an ice bath, there is slowly added 25.3 ml (0.2048 moles) of 2-methyl-1-pentanol, diluted with an equal volume of cyclohexane. The reaction proceeds smoothly with vigorous gas evolution, but no spattering on the walls of the flask, to give a crystal-clear, water-white, somewhat viscous solution. Titration of the resulting solution for Mg shows the solution to contain 0.66 moles of magnesium per liter of solution.

A 2 ml sample of the solution is treated with about 0.5 ml of neat titanium tetra-isopropylate, resulting in an immediate gelation, but no color change, indicating reaction of all alkyl groups with the alcohol.

The viscosity of the magnesium 2-methyl-1-pentyloxide solution is noticeably reduced by the addition of 1.2 ml (0.01 moles) of 2-methyl-1-pentanol.

(b) To a volume of 10 ml of 1.156 Molar n-butyl-sec-butyl-magnesium (11.56 mmoles) there is added 1.43 ml (11.56 mmoles) of 2-methyl-1-pentanol, diluted to 5 ml with heptane. Then, 0.6 ml of 0.99 Molar (0.59 mmoles) of potassium tert-amylate in cyclohexane solution is added, followed by an additional 1.43 ml of 2-methyl-1-pentanol (11.56 mmoles). A pale yellow, clear, slightly viscous solution of magnesium 2-methyl-1-pentyloxide is obtained. No excess of 2-methyl-1-pentanol is added as in comparative Example I(a).

(c) To 10 ml of a solution of 4.33 ml of 2-methyl-1-pentanol in heptane there is added 0.4 ml of 1.91 Molar n-butyllithium in cyclohexane. To the cloudy mixture, there is added, slowly and with good mixing, 15 ml of a 1.036 Molar solution of n-butyl-sec-butylmagnesium in heptane. A clear, colorless, viscous solution of magnesium 2-methyl-1-pentyloxide is obtained.

COMPARATIVE EXAMPLE I-A

To a volume of 100 ml of 1.024M DBM solution in heptane there is slowly added 25.3 ml (20.9 g, 0.2048 moles) of neat 2-methyl-1-pentanol while stirring and cooling in an ice bath. Vigorous gas evolution occurs, with spattering of viscous, gel-like material on the walls of the flask. The main body of the solution remains fluid, at least through the half-way point in the addition of the alcohol. After this point is reached, the solution becomes increasingly viscous, then gels near the end of the addition to a clear solid mass. A volume of 100 ml of cyclohexane is added, but the gel does not dissolve. The mixture is heated to reflux; but, again, no thinning or solution of the product occurs. Next, 50 ml of toluene is added, again with no effect. Finally, two consecutive 15 ml (0.1 mole) additions of TMEDA is made, also with little or no effect. The mix is decomposed by pouring the heavy, viscous, taffy-like mass into ice water.

Example I(a) shows the beneficial effect of the addition of a very small amount of trialkylaluminum to the DBM prior to its reaction with 2-methyl-1-pentanol, while Examples I(b) and (c) show the beneficial effects of the addition of a small amount of potassium or lithium alkoxide during the reaction.

COMPARATIVE EXAMPLE I-B

To a solution of 104 ml of 2-methyl-1-pentanol (0.84 moles) in 180 ml of chlorobenzene there is added 13.2 ml of an 0.92M solution of TIBAL in heptane (t = 25°). After reaction is complete, a volume of 252 ml of a 1.6M solution of n-butyl-sec-butylmagnesium in heptane is slowly added over a 40-minute period, the temperature of the solution rising to 90°. The clear, colorless, viscous solution is cooled to 25° and 110 ml of heptane is added, along with an additional 2 ml of 0.92M TIBAL.

Assay of the solution for magnesium content shows a content of 0.67 moles per liter.

This Example shows that the TIBAL can be prereacted with the alcohol before reaction with dibutylmagnesium.

EXAMPLE II

Preparation of Hydrocarbon-Soluble Magnesium 2-Ethyl-1-Hexyloxide (Hexanolate)

To 10 ml of 1.355M di-n-hexylmagnesium in cyclohexane (already containing 3 mole % TIBAL based on contained Mg) is added, dropwise, 4.24 ml (3.53 g, 0.027 moles) of neat 2-ethyl-1-hexanol. No visible precipitate appears at any point during the addition. The solution is heated to reflux briefly and cooled to room temperature in a cold water bath. Then 5 ml of cyclohexane is added to give a crystal-clear, water-white, quite viscous solution containing approximately 0.9 moles Mg/liter (1.8N). Further dilution with 10 ml of cyclohexane decreases the viscosity somewhat. Addition of 3 mmoles of aluminum isopropoxide in solution in cyclohexane does not reduce the viscosity further; nor does the addition of 1 mmole of TIBAL. Addition of 1 ml (0.006 mole) of neat 2-ethyl-1-hexanol significantly reduces the viscosity.

EXAMPLE III

Preparation of Hydrocarbon-Soluble Magnesium 2-Ethyl-4-Methyl-1-Pentyloxide (Pentanolate)

To 10 ml of 1.085M DBM solution in heptane is added 0.33 ml of 0.92M TIBAL. Then, 3.4 ml (21.7 mmoles) of 2-ethyl-4-methyl-1-pentanol, diluted to 5 ml with cyclohexane, is slowly added, dropwise, to the organometallic solution. Reaction proceeds smoothly, with vigorous evolution of butane. No precipitate or gel forms during any part of the alcohol addition. On cooling to room temperature, hazing and incipient crystallization begins. Addition of 0.39 ml of 2-methyl-1-pentanol (3 mmoles) dissolves all solids and gives a crystal-clear solution. After standing for 3 days, the solution sets up to a clear, hard gel which dissolves to a clear viscous solution on heating to 55° in a water bath. A volume of 3.5 ml of 0.92M TIBAL in heptane (3.2 mmoles) is added, followed by 0.85 ml (6.9 mmoles) of 2-methylpentanol. A clear, fluid solution results on cooling to room temperature.

EXAMPLE IV

Preparation of Hydrocarbon-Soluble Mixed Alkoxides of Magnesium 2-Methyl-1-Pentyloxide and Magnesium Isopropoxide (a) From (2:1) 2-Methyl-1-Pentanol/Isopropanol To 10 ml of 1.085M DBM in heptane containing 0.33 ml of 0.92M TIBAL is added slowly a mixture of 2-methyl-1-pentanol (1.80 ml, 14.45 mmoles) and isopropanol (0.55 ml, 7.25 mmoles) diluted to 5 ml with cyclohexane. The solution remains clear throughout the addition (no precipitate formation) and is crystal-clear and somewhat viscous at room temperature.

(b) From (1:1) 2-Methyl-1-Pentanol/Isopropanol

To 10 ml of 1.085M DBM in heptane and 0.33 ml of 0.92M TIBAL (as above) is slowly added a mixture of 2-methyl-1-pentanol (1.34 ml, 10.85 mmoles) and isopropanol (0.82 ml, 10.85 mmoles) diluted to 5 ml with cyclohexane. Again, a clear, stable solution results at room temperature.

(c) From (1:2) 2-Methyl-1-Pentanol/Isopropanol

To 10 ml of 1.085M DBM in heptane and 0.33 ml of 0.92M TIBAL (as above) is slowly added a mixture of 2-methyl-1-pentanol (0.9 ml, 7.25 mmoles) and isopropanol (1.1 ml, 14.45 mmoles), diluted to 5 ml with cyclohexane. A slurry is formed which dissolves on addition of 0.9 ml (7.25 mmoles) of 2-methyl-1-pentanol.

EXAMPLE V

Preparation of a Hydrocarbon-Soluble Complex of Magnesium 2-Ethyl-1-Butoxide and Magnesium Isoproxide To 10 ml of 1.085M DBM in heptane and 0.33 ml of 0.92 TIBAL is slowly added a mixture of 2-ethyl-1-butanol (1.33 ml, 10.85 mmoles) and isopropanol (0.82 ml, 10.85 mmoles) diluted to 5 ml with cyclohexane. The reaction mixture is a clear solution at 50°, which becomes hazy on cooling. Addition of 0.39 ml (3 mmoles) of 2-methyl-1-pentanol produces a stable, crystal-clear solution.

EXAMPLE VI

Preparation of a Hydrocarbon-Soluble Complex of Magnesium 2-Methylpentyloxide and Magnesium tert-Butoxide To 10 ml of a 1.085M n-butyl-sec-butylmagnesium solution in heptane, containing 0.33 ml of 0.92M TIBAL in heptane, is added, slowly, a mixture of 2-methyl-1-pentanol, 1.34 ml (10.85 mmoles) and tert-butanol, 1.02 ml (10.85 mmoles) diluted to 5 ml with cyclohexane. The solution remains slightly hazy throughout the alcohol addition, but essentially remains mobile and clear throughout. Addition of 0.3 ml (2.4 mmoles) of 2-methylpentanol to this solution results in a stable, water-clear, slightly viscous solution.

EXAMPLE VII

Preparation of a Hydrocarbon-Soluble Complex of Magnesium 2-Methylpentyloxide and Magnesium n-Butoxide A mixture of 1.34 ml (10.85 mmoles) of 2-methyl-1-pentanol and 0.99 ml (10.85 mmoles) of n-butanol diluted to 5 ml with cyclohexane is added slowly to a solution of 10 ml of 1.085M n-butyl-sec-butylmagnesium in heptane and 0.33 ml of 0.92M TIBAL in heptane. The solution remains clear to the halfway point in the alcohol addition, after which a heavy solid gel gradually forms. Then 5 ml of cyclohexane and 0.45 ml of 2-methyl-1-pentanol are added and the mixture is heated to 50°-60° for several hours. The gelatinous solids gradually dissolve to give a somewhat viscous, mobile, crystal-clear solution. On cooling to room temperature, the viscosity increases to the point where the solution flows only very slowly. Addition of 0.92 ml of 0.92M TIBAL in heptane produces a completely fluid solution.

EXAMPLE VIII (a) Preparation of Hydrocarbon-Soluble Magnesium 2-Ethoxyethoxide To 10 mmoles of a DBM solution in 10 ml of heptane there is added, dropwise, 21 mmoles (2.0 ml) of 2-ethoxyethanol ("Cellosolve") diluted to 5 ml with heptane. A hazy, quite mobile solution is obtained, which, on centrifugation, gives 12 ml of a clear, water-white, non-viscous solution containing 0.825 mmoles of magnesium per ml of solution (analysis by EDTA titration) representing essentially all of the initial magnesium reagent.

(b) Preparation of Hydrocarbon-Soluble Magnesium 2-Hexyloxy-1-Ethoxide

Reaction of 10 mmoles of DBM solution, as above, with 21 mmoles of Hexyl "Cellosolve" (2-hexyloxyethanol) gives a crystal-clear, water-white, completely fluid solution.

(c) Preparation of Hydrocarbon-Soluble Magnesium-2-Ethoxyethoxide 68.6 g (0.6 moles) of solid magnesium ethoxide, $Mg(OC_2H_5)_2$ is mixed with 120 ml of heptane and 112 ml (1.15 moles) of 2-ethoxyethanol, with stirring. As the mixture is stirred the temperature slowly rises to about 40° over a period of 15 minutes, then drops off to below 30° within the next hour. The mixture is then stirred for a period of 3 hours during which most of the contained solids dissolve. The resulting mixture is filtered, and the clear filtrate diluted with an additional 160 ml of heptane. Analysis of the solution shows it to contain 1.16 moles of magnesium per liter.

(d) Preparation of Hydrocarbon-Soluble Magnesium 2-Ethoxyethoxide 7.3 g of magnesium metal chips and 64 ml of "Cellosolve" are placed together in a flask, a few crystals of iodine added, and the mixture reacted at 70°–80° C. for 18 hours. A light, creamy, viscous mass results, which is readily dissolved in 30 ml of chlorobenzene to give a 2.09 Molar solution.

(e) Preparation of a Liquid Magnesium 2-Ethoxyethoxide Product Complexed with Ethanol To 34.3 g (0.3 moles) of magnesium ethoxide (Mg(OEt)$_2$) is added 61 ml of "Cellosolve" (2-ethoxyethanol) and the mixture stirred. After about 15 minutes, the temperature rises to 40°, and most of the Mg(OEt)$_2$ goes into solution. The mix is heated to 50° for 1 hour, then allowed to cool and settle. The dark, greyish-black liquid is analyzed for magnesium content and found to be 3.32 Molar in Mg. The product is soluble in chlorobenzene and heptane.

EXAMPLE IX

Preparation of Maqnesium 2-n-Hexyloxy-1-Ethoxide 34.5 g (0.3 moles) of magnesium ethoxide, 104 ml, 92 g (0.63 moles) of n-Hexyl "Cellosolve", and 200 ml of heptane are stirred together for 5 hours at room temperature. Most of the solids dissolve, except for some grey fines. The product solution is filtered, and the filtrate is analyzed for magnesium content. Found: 0.92 Moles Mg/liter.

EXAMPLE X

Preparation of a Hydrocarbon-Soluble Complex of Magnesium 2-Ethoxyethoxide and Magnesium 2-Hexyloxyethoxide 80 ml of an 0.82 Molar solution of magnesium 2-ethoxyethoxide in heptane and 75 ml of the product solution of EXAMPLE IX are combined, stirred thoroughly, then stripped of solvent, and heated to 125°–130° C. for 2.5 hours under full vacuum. The residual product is a clear, viscous liquid at this temperature.

On cooling to room temperature, the product solidifies to a clear glass, which is readily dissolved in 50 ml of methylcyclohexane.

EXAMPLE XI

Preparation of a Hydrocarbon-Soluble Complex of Sodium Trihexylmagnesiate and Magnesium 2-Methyl-1-Pentyloxide A 6 ml portion of the heptane-cyclohexane solution of magnesium 2-methyl-1-pentyloxide (3.9 mmoles) of Example I is added to 9.5 ml of a 0.4M (3.8 mmoles) solution of sodium tri-n-hexylmagnesiate in cyclohexane. A clear, colorless solution of an approximately 1:1 complex of sodium tri-n-hexyl magnesiate and magnesium 2-methyl-1-pentyloxide, NaMgHex$_3$D.Mg(O-3MP)$_2$, is obtained (2MP = 2-Methylpentyl). Alternatively, this complex can be written as NaHex.[HexMg-O-2MP]$_2$.

EXAMPLE XII

Preparation of a Hydrocarbon-Soluble Complex of Triisobutylaluminum (TIBAL) and Magnesium 2-Methyl-1-Pentyloxide A 10 ml portion of the heptane-cyclohexane solution of magnesium 2-methyl-1-pentyloxide (6.6 mmoles) of Example I is added to 7.3 ml of a 0.92M solution (6.6 mmoles) of TIBAL in heptane. A clear, colorless solution of an approximately 1:1 Molar complex of triisobutylaluminum and magnesium 2-methyl-1-pentyloxide is obtained (Mg(O-2MP)$_2$.Al(IsoBu)$_3$). Alternatively, this complex can be written as MgAl(O-2MP)$_2$.(IsoBu)$_3$ or IsoBuMg-O-2MP.(IsoBu)$_2$Al(O-2MP).

EXAMPLE XIII

Preparation of a Hydrocarbon-Soluble Complex of 1,3-bis-(1-Lithio-1,3-Dimethylpentyl) Benzene and Magnesium 2-Methyl-1-Pentyloxide To 6.5 ml of a 1.03N (0.515M) solution of 1,3-bis-(1-lithio-1,3-dimethylpentyl) benzene (DILIBID) in cyclohexane, containing 1 molar equivalent of triethylamine per carbon lithium bond, is added 5 ml of a 0.66M solution of magnesium 2-methylpentyloxide. A fluid, deep-red-colored solution of the 1:1 molar complex of DILIBID and magnesium 2-methylpentyloxide results. Addition of another molar equivalent of magnesium 2-methylpentyloxide results in a fluid solution of the 1:2 Molar complex.

EXAMPLE XIV

Preparation of a Hydrocarbon-Soluble Complex of n-Butylsodium, n-Butyllithium and Magnesium 2-Methylpentyloxide A weight of 0.77 g (8 mmoles) of sodium tert-butoxide is suspended in 5 ml of heptane and 7 ml of 1.66M n-butyllithium (12 mmoles) in hexane is added. After reaction, the solids are filtered and washed thoroughly with heptane. To the solids is then added 18 ml of a solution of 13.2 mmoles of n-butyllithium and 6.6 mmoles of magnesium 2-methylpentyloxide in toluene. The solids dissolve on shaking, yielding a pale yellow solution containing a product of the approximate composition: (n-BuLi)$_2$.n-BuNa.[Mg(O-2MP)$_2$]$_2$.

EXAMPLE XV

Preparation of a Hydrocarbon-Soluble Complex of Potassium tert-Butoxide and Magnesium 2-Methyl-1-Pentyloxide To 0.74 grams (6.6 mmoles) of solid potassium tert-butoxide there is added 10 ml of 0.66 Molar magnesium 2-methyl-1-pentyloxide in heptane. The product thickens to a gel; then, on further mixing, thins out to form a completely clear, fluid, pale yellow solution having the composition KOt-Bu-Mg(O-2MP)$_2$ or KMg(O-2MP)$_2$(O-tert-Bu).

EXAMPLE XVI

Preparation of a Hydrocarbon-Soluble Complex of Sodium 2-Methyl-1-Pentyloxide and Magnesium 2-Methyl-1-Pentyloxide To 10 ml of a 0.4 Molar solution of sodium tri-n-hexyl-magnesiate in cyclohexane there is added, incrementally, three 0.5 ml portions of 2-methyl-1-pentanol. The solution remains clear after each addition. The final product (NaMg(O-2MP)$_3$) is a clear, colorless, highly fluid solution.

EXAMPLE XVII

Preparation of a Hydrocarbon-Soluble Complex of Lithium 2-Methyl-1-Pentyloxide and Magnesium 2-Methyl-1-Pentyloxide To a solution of 5 ml of 1.6 Molar n-butyl-sec-butyl-magnesium in heptane and 4.2 ml of 1.9 Molar n-butyllithium in cyclohexane there is added, incrementally, three 1.0 ml portions of 2-methyl-1-pentanol. The solution remains clear after each addition. During the addition of the last 1.0 ml increment, the solution becomes quite thick, then thins out on further mixing. An additional 10 ml of heptane is added. A clear, colorless, slightly viscous solution of LiMg(O-2MP)$_3$ is obtained.

EXAMPLE XVIII

Preparation of a Complex of a Hydrocarbon-Soluble Magnesium Dialkoxide and a Dialkylmagnesium Compound A 10 ml portion of the heptane-cyclohexane solution of magnesium 2-methyl-1-pentyloxide (6.6 mmoles) of Example I is mixed with 6.1 ml of 1.085M DBM solution in heptane. A clear solution of the 1:1 Molar complex of magnesium 2-methyl-1-pentyloxide and n-butyl-sec-butylmagnesium is obtained. Assuming total scrambling of alkyl and alkoxy groups, this complex can be represented as (n,s)-butylmagnesium 2-methylpentyloxide. The complex can also be prepared by the addition of 13.2 mmoles (1.63 ml) of neat 2-methyl-1-pentanol to 13.2 mmoles (12.2 ml) of 1.085M DBM solution in heptane.

EXAMPLE XIX

Preparation of a Complex of a Hydrocarbon-Soluble Magnesium Alkoxide and an Alkyllithium Compound A 10 ml portion of the heptane-cyclohexane solution of magnesium 2-methyl-1-pentyloxide (6.6 mmoles) of Example I is added to 3.5 ml of 1.92M n-butyllithium in 5 ml of cyclohexane to give a crystal-clear, mobile, colorless solution of the 1:1 complex of n-butyllithium and magnesium 2-methyl-1-pentyloxide (n-BuLi.Mg(O-2MP)$_2$) (2MP=2-Methylpentyl). Alternatively, this complex may be written as LiMg(O-2MP)$_2$(Bu).

I claim:

1. In a process for the preparation of hydrocarbon- or chlorinated hydrocarbon- solvent solutions of magnesium dialkoxides, the steps which comprise reacting a suspension of magnesium metal or magnesium amide, or a solution of a dialkylmagnesium compound in a volatile hydrocarbon or chlorinated hydrocarbon solvent with an alcohol selected from the group of (a) aliphatic 2-alkyl-substituted C$_4$–C$_{12}$ primary monohydric alcohols; or (b) mixtures of said (a) alcohols with C$_3$–C$_{12}$ aliphatic secondary or tertiary alcohols; or (c) mixtures of said (a) alcohols with C$_1$–C12 aliphatic primary linear unsubstituted alcohols; the mole ratios of said (a) to said (b), and said (a) to said (c), alcohols being 1 of said (a) alcohols to 0.1 to 2 of said (b) and said (c) alcohols; and removing hydrogen or ammonia which forms during the reaction.

2. The process of claim 1, in which the (a) alcohol is at least one member selected from the group of isobutyl alcohol, 2-methyl-1-pentanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol and 2-ethyl-5-methyl-1-octanol.

3. The process of claim 1, in which the C$_3$–C$_{12}$ alcohol which is mixed with the (a) alcohols to constitute the (b) mixtures is at least one member selected from the group of isopropanol, sec-butanol, 4-methyl-2-pentanol, tert-butanol, tert-amyl alcohol, 3-methyl-3-pentanol, and 2,6-dimethyl-4-pentanol.

4. The process of claim 1, in which the C$_1$–C$_{12}$ alcohol which is mixed with the (a) alcohols to constitute the (c) mixture is at least one member selected from the group of methanol, ethanol, n-propanol, n-butanol, n-hexanol and n-octanol.

5. The process of claim 1, in which the dialkylmagnesium compound is selected from the group of n-butyl-sec-butyl magnesium, n-butyl-ethylmagnesium, di-n-hexylmagnesium, n-butyl-n-octylmagnesium, and mixed ethyl, butyl, hexyl and octylmagnesiums.

6. The process of claim 1, in which there is included in the reaction mixture a minor amount of a complexing solubilizer in the form of a member selected from the group consisting of trialkylaluminum compounds and alkyllithium compounds.

7. The process of claim 1, in which there is included in the reaction mixture a minor amount of a complexing solubilizer selected from the group of alkali metal alkoxides.

8. The process of claim 1, in which an excess of said (a) alcohols or said mixtures thereof with said (b) and (c) alcohols, above that necessary to react with all of the dialkylmagnesium present, is employed, the excess of said alcohol or alcohols being in the range of 0.01 to 2 moles of alcohol per mole of magnesium reacted.

9. The process of claim 6, in which the amount of the trialkylaluminum compound, which is complexed with the dialkylmagnesium present, is in the range of 0.01 to 0.1 moles per mole of the dialkylmagnesium.

10. The process of claim 7, in which the alkali metal alkoxide is potassium alkoxide, and the amount of said potassium alkoxide, which is complexed with dialkylmagnesium, is in the range of 0.01 to 0.1 mole per mole of the dialkylmagnesium.

11. The process of claim 6, in which the alkyllithiums are n-alkyllithiums, and the amount of said n-alkyllithium, which is complexed with the dialkylmagnesium, is in the range of 0.01 to 0.1 mole per mole of the dialkylmagnesium.

12. The process of claim 7, in which the said alkali metal alkoxides are selected from the group of lithium isopropoxide, lithium sec-butoxide, lithium tert-butoxide, lithium 2-methyl-1-pentyloxide, sodium tert-butoxide, sodium tert-amyloxide, sodium 2-methyl-1-pentyloxide, potassium tert-butoxide, potassium tert-amyloxide and potassium 2-methyl-1-pentyloxide, and the amount of said metal alkoxides complexed with dialkylmagnesium is in the range of 0.01 to 0.1 mole per mole of dialkylmagnesium.

13. The process of claim 1, which includes the step, after the removal of the hydrogen or ammonia, of reacting the resulting reaction product, in a liquid hydrocarbon or chlorinated hydrocarbon, with at least one member selected from the group of alkyllithiums, dialkylmagnesiums and trialkylaluminums in which the alkyl radicals contain from 2 to 18 carbon atoms to form a hydrocarbon-soluble complex with the magnesium dialkoxide, and the mole ratio is 0.01 to 1 of said alkyllithiums, dialkylmagnesiums and trialkylaluminums per mole of the magnesium dialkoxide.

14. The process of claim 13, in which the alkyllithiums, diakylmagnesiums and trialkylaluminums are selected from the group of n-butyllithium, sec-butyllithium, n-butyl-sec-butylmagnesium, butyloctylmagnesium, butylethylmagnesium, triethylaluminum, triisobutylaluminum and tri-n-butylaluminum, the amount of said compounds complexed with magnesium alkoxide being in the range of 0.1 to 10 miles per mole of said alkoxide.

15. In a process for the preparation of hydrocarbon or chlorinated hydrocarbon solvent-soluble magnesium dialkoxides, the steps which comprise reacting a suspension of magnesium metal, or magnesium amide or $C_1$–$C_3$ magnesium alkoxides in a volatile hydrocarbon or chlorinated hydrocarbon solvent, or a solution of a dialkylmagnesium compound in said solvent, with a 2-alkoxy-substituted-1-alkanol (ROCH$_2$CHR'OH) where R is a $C_1$–$C_3$ hydrocarbyl and R' is hydrogen or $C_1$–$C_3$ hydrocarbyl; or a member of the group of $\gamma$-akoxy-poly(ethylene-oxy)-1-ethanols RO(CH$_2$CH$_2$O)$_n$CH$_2$CH$_2$OH where R is a $C_1$–$C_{12}$ hydrocarbyl group and n is from 0 to 4; or a mixture thereof with each other or with any of the alcohols selected from those recited in claim 1; and removing hydrogen or ammonia which results from the reaction.

16. The process of claim 15, in which said 2-alkoxy-substituted-1-alkanols are selected from the group of 2-methoxy-1-ethanol, 2-ethoxy-1-ethanol, 2-butoxy-1-ethanol and 2-hexyloxy-1-ethanol.

17. The process of claim 15, in which said $\gamma$-alkoxy-poly(ethylenoxy)-1-ethanols are selected from the group of 2-ethoxyethoxy-1-ethanol, 2-butoxyethoxy-1-ethanol and 2-hexyloxyethoxy-1-ethanol.

18. A process for the preparation of hydrocarbon or chlorinated hydrocarbon solvent solutions of magnesium 2-alkoxyalkoxides, which comprises reacting a solid magnesium dialkoxide of the formula Mg(OR)$_2$ in which R is a $C_1$–$C_{12}$ hydrocarbyl group, with at least two molar equivalents of a 2-alkoxy-substituted-1-alkanol, ROCH$_2$CHR'OH, where R is a $C_1$–$C_{12}$ hydrocarbyl group and R' is hydrogen or $C_1$–$C_3$ hydrocarbyl group, isolating the resultant mobile liquid product, and dissolving same in a hydrocarbon or chlorinated hydrocarbon solvent.

19. A process for the preparation of hydrocarbon or chlorinated hydrocarbon solvent solutions of magnesium 2-alkoxyalkoxides, which comprises reacting magnesium metal with at least two molar equivalents of a 2-alkoxy-substituted-1-alkanol, ROCH$_2$CHR'OH, or mixtures of such alkanols, in which R is a $C_1$–$C_{12}$ hydrocarbyl group and R' is H or $C_1$–$C_3$ hydrocarbyl group, and then dissolving the product in a hydrocarbon or chlorinated hydrocarbon solvent.

20. A process for the preparation of hydrocarbon or chlorinated hydrocarbon solvent solutions of magnesium 2-alkoxyalkoxides, which comprises reacting dialkylmagnesium compounds of the formula MgR$_2$ in which R is a $C_1$–$C_{12}$ hydrocarbyl group, with at least two molar equivalents of a 2-alkoxy-substituted-1-alkanol, ROCH$_2$CHR'OH, or mixtures of such alkanols, in which R is a $C_1$–$C_{12}$ hydrocarbyl group and R' is hydrogen or a $C_1$–$C_3$ hydrocarbyl group.

21. A chemical composition selected from the group consisting of liquid hydrocarbon or chlorinated hydrocarbon solvent-soluble compounds and complexes of (i) magnesium aliphatic 2-alkyl-substituted $C_4$–$C_{12}$ primary, (normal) dialkoxides, (ii) mixtures of magnesium 2-alkyl-substituted $C_4$–$C_{12}$ primary (normal) dialkoxides with very minor proportions of magnesium aliphatic $C_3$–$C_{12}$ secondary alkoxides, (iii) mixtures of magnesium aliphatic 2-alkyl-substituted $C_4$–$C_{12}$ primary (normal) dialkoxides with very minor proportions of magnesium aliphatic $C_4$–$C_{12}$ tertiary alkoxides, and (iv) mixtures of magnesium aliphatic 2-alkyl-substituted $C_4$–$C_{12}$ primary (normal) dialkoxides with very minor proportions of magnesium linear $C_1$–$C_{12}$ primary (normal) alkoxides.

22. A chemical composition selected from the group consisting of liquid hydrocarbon or chlorinated hydrocarbon solvent-soluble compounds and complexes of (i) magnesium 2-methylpentyloxide, (ii) magnesium 2-ethylhexyloxide, (iii) magnesium 2-methylpentyloxide and magnesium isopropoxide, (iv) magnesium 2-methylpentyloxide and magnesium tert-butoxide, and (v) magnesium 2-methyl-pentyloxide and magnesium n-butoxide.

23. The chemical composition of claim 22, in which the mole ratio of magnesium 2-methylpentyloxide to each of the other alkoxides in said respective complexes is in the range of from about 1:3 to about 3:1.

24. A product soluble in hydrocarbon or chlorinated hydrocarbon solvents selected from the group of magnesium 2-alkoxy-1-alkoxides, Mg(OCH(R')CH$_2$OR)$_2$.(R"OH)$_x$ in which R and R" are $C_1$–$C_{12}$ hydrocarbyl groups, R' is hydrogen or $C_1$–$C_3$ hydrocarbyl group, and x is 0.01 to 2 excess moles per mole of magnesium dialkoxide, said product serving as a precursor for the information of catalyst substrates used in alpha olefin polmerizations.

25. A product selected from the group of magnesium $\gamma$-akoxy-poly(ethyleneoxy)-1-ethoxides, Mg(OCH$_2$CH$_2$(OCH$_2$CH$_2$)$_n$OR)$_2$.(R'OH)$_x$ in which R and R' are $C_1$–$C_{12}$ hydrocarbyl groups, n=0–4, and x=0.01 to 2 excess moles per mole of magnesium dialkoxide, said product being soluble in hydrocarbon or chlorinated hydrocarbon solvents, said product serving as a precursor for the formation of catalysts substrates used in alpha olefin polymerization.

26. A composition according to claim 24, in which the magnesium 2-alkoxy-1-alkoxide is magnesium 2-ethoxyethoxide, the alcohol of complexation (solvation) is ethanol and x is 2, said composition existing as a mibile liquid at ordinary temperatures and in the absence of added solvents.

27. A product according to claim 24, in which a mixture of two magnesium 2-alkoxy-1-akoxides is cogenerated, the mixture consisting of a 1:1 molar complex of magnesium 2-ethoxyethoxide and magnesium 2-hexyloxyethoxide, said mixture being free of solvent and existing as a liquid at elevated temperature.

28. An organometallic complex composition soluble in a volatile liquid hydrocarbon or chlorinated hydrocarbon solvent comprising (i) at least one member selected from the group of alkyllithiums, trialkylaluminums and dialkylmagnesiums soluble in hydrocarbon solvents or chlorinated hydrocarbon solvents in which the alkyl group or groups contain from 2 to 18 carbon atoms reacted with (ii) a magnesium dialkoxide dissolved in a hydrocarbon or chlorinated hydrocarbon solvent, the alcoholic moiety of said dialkoxide being derived from alcohols selected from the group of (a) aliphatic 2-alkyl-substituted $C_4$–$C_{12}$ primary monohydric alcohols; or (b) mixtures of said (a) alcohols with $C_3$–$C_{12}$ aliphatic secondary or tertiary alcohols; or (c) mixtures of said (a) alcohols with $C_1$–$C_{12}$ aliphatic primary linear unsubstituted alcohols; the mole ratios of said (a) to said (b), and said (a) to said (c), alcohols being 1 of said (a) alcohols to 0.1 to 2 of said (b) and said (c) alcohols, said composition being substantially free from ammonia.

29. A composition according to claim 28, in which the alkyl radical of said (a) alcohol contains from 4 to 8 carbon atoms.

30. A composition according to claim 28, in which the alcohol is at least one member selected from the group of isobutyl alcohol, 2-methy-1-pentanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, and 2-ethyl-5-methyl-1-octanol.

31. A composition according to claim 28, in which the trialkylaluminum is triisobutylaluminum and the magnesium dialkoxide is magnesium 2-methyl-1-pentyloxide.

32. A composition according to claim 28, in which the alkyllithium is n-butyllithium and the magnesium dialkoxide is magnesium 2-methyl-1-pentyloxide.

33. A composition according to claim 28, in which the dialkylmagnesium is n-butyl-sec-butylmagnesium and the magnesium dialkoxide is magnesium 2-methyl-1-pentyloxide.

34. A chemical complex selected from the group of liquid hydrocarbon or chlorinated hydrocarbon solvent-soluble complexes of
(i) Magnesium 2-methylpentyloxide and n-butyl-sec-butylmagnesium;
(ii) Magnesium 2-methylpentyloxide and n-butyllithium;
(iii) Magnesium 2-methylpentyloxide and triisobutylaluminum;
(iv) Magnesium 2-methylpentyloxide and sodium tri-n-hexylmagnesiate;
(v) Magnesium 2-methylpentyloxide, n-butyllithium and n-butylsodium;
(vi) Magnesium 2-methylpentyloxide and lithium 2-methylpentyloxide;
(vii) Magnesium 2-methylpentyloxide and potassium 2-methylpentyloxide.

35. An organometallic complex composition soluble in hydrocarbon or chlorinated hydrocarbon solvent solutions which is useful for the preparation of polymerization catalysts or initiators, said composition being produced by reacting a member selected the group consisting of alkyllithiums, alkylsodiums, trialkylaluminums and dialkylmagnesiums and mixtures thereof soluble in hydrocarbon or chlorinated hydrocarbon solvents with a volatile hydrocarbon or chlorinated hydrocarbon solvent solution of a magnesium dialkoxide resulting from the reaction of a mixture of magnesium metal, magnesium amide or a solution of a dialkylmagnesium compound in a volatile hydrocarbon or chlorinated hydrocarbon solvent, with a minor amount of a trialkylaluminum, n-alkyllithium or potassium alkoxide and with alcohols as such or in solution in a volatile liquid hydrocarbon or chlorinated hydrocarbon, said alcohols selected from the group of (a) aliphatic 2-alkyl-substituted $C_4$–$C_{12}$ primary monohydric alcohols; or (b) mixtures of said (a) alcohols with $C_3$–$C_{12}$ aliphatic secondary or tertiary alcohols; or (c) mixtures of said (a) alcohols with $C_1$–$C_{12}$ aliphatic primary linear unsubstituted alcohols; the mole ratios of said (a) to said (b), and said (a) to said (c), alcohols being 1 of said (a) alcohols to 0.1 to 2 of said (b) and said (c) alcohols, said composition being essentially free from hydrogen or ammonia which formed during the reaction.

36. A magnesium dialkoxide complex product soluble in hydrocarbon or chlorinated hydrocarbon solvents, comprising the reaction product of a suspension of (a) magnesium metal, or magnesium amide, or $C_1$–$C_3$ magnesium alkoxides in a volatile hydrocarbon or chlorinated hydrocarbon solvent, or a solution of a dialkylmagnesium compound in said solvent, with (b) a 2-alkoxy-substituted-1-alkanol ($ROCH_2CHR'OH$) where R is a $C_1$–$C_{12}$ hydrocarbyl and R' is hydrogen or $C_1$–$C_3$ hydrocarbyl, or a member of the group of γ-alkoxy-poly(ethylene-oxy)-1-ethanols ($ROCH_2CH_2O)_nCH_2CH_2OH$ where R is a $C_1$–$C_{12}$ hydrocarbyl group and n is from 0 to 4, or a mixture thereof with each other or with any of the alcohols selected from those recited in claim 1, the alcohols in said product being present in the range of 0,01 to 2 excess moles per mole of the magnesium dialkoxide.

* * * * *